United States Patent [19]

Ohsawa

[11] Patent Number: 5,530,780
[45] Date of Patent: Jun. 25, 1996

[54] FIBER OPTIC LASER CONDUCTING AND DIFFUSION DEVICE

[75] Inventor: Masami Ohsawa, Saitama-ken, Japan

[73] Assignees: Lederle (Japan), Ltd., Tokyo; Hamamatsu Photonics K.K., Shizuoka-ken; Moritex Corp., Tokyo, all of Japan

[21] Appl. No.: 473,931

[22] Filed: Jun. 7, 1995

Related U.S. Application Data

[63] Continuation-in-part of Ser. No. 358,258, Dec. 19, 1994, abandoned.

[30] Foreign Application Priority Data

Dec. 20, 1993 [JP] Japan .................... 5-075579 U

[51] Int. Cl.⁶ .................................................. G02B 6/26
[52] U.S. Cl. ........................................... 385/31; 385/901
[58] Field of Search ........................... 606/7, 8, 14, 15, 606/16, 18; 385/31, 33, 34, 35, 79, 139, 901

[56] References Cited

U.S. PATENT DOCUMENTS

| | | | |
|---|---|---|---|
| 5,209,748 | 5/1993 | Daikuzono | 606/16 |
| 5,303,324 | 4/1994 | Lundahl | 385/901 |

FOREIGN PATENT DOCUMENTS

| | | | |
|---|---|---|---|
| 3833991 | 4/1990 | Germany | 385/38 |
| 3833990 | 4/1990 | Germany | 385/38 |

*Primary Examiner*—John Ngo
*Attorney, Agent, or Firm*—Wenderoth, Lind & Ponack

[57] ABSTRACT

A polyolefin resin light diffusion tip is attached to an optical fiber end for conducting a pulse laser beam.

10 Claims, 2 Drawing Sheets

FIBER OPTIC LASER CONDUCTING AND DIFFUSION DEVICE

This application is a continuation-in-part of now abandoned application, Ser. No. 08/358,258, filed Dec. 19, 1994.

BACKGROUND OF THE INVENTION AND PRIOR ART

The present invention relates to a fiber optic laser conducting and diffusion device used for a laser dynamic therapy for an early cancer, the laser dynamic therapy known as a photodynamic therapy.

The laser dynamic therapy for an early cancer is performed, while observing the body cavity by an endoscope, irradiating a laser beam in the amount as necessary against the affected part by a fiber optic laser conducting and diffusion device inserted through a forceps aperture of the endoscope. Particularly, it is necessary to provide at the extreme end of the device a tip capable of carrying out the irradiation of a laser beam in response to shapes of the body cavity such as tubular organs such as a throat and a cervical canal, and bag-like organs such as a stomach and kidney. For that purpose, methods heretofore proposed include U.S. Pat. Nos. 4,693,556 and 4,660,925 in which a tip is formed at the extreme end by an ultraviolet hardening resin containing a fine powder of quartz to provide a uniform diffusion of light; U.S. Pat. No. 4,676,231 in which a transparent liquid with fine particles suspended is put into a hollow transparent tip; and U.S. Pat. No. 4,646,151 which suggests in its specification and drawings that an epoxy resin mixed with light diffusion particles is coated on an internal surface of a hollow transparent tip.

In case a pulse wave laser beam is used, an end tip formed of an inorganic material (Examples: quartz, sapphire, glass, etc.) tends to be easily cracked and broken, which is dangerous, when the concentration and high densification of shock waves generated from a pulse laser occur. A similar situation tends to occur in a tip which uses hard plastics (Examples: polymethylmethacrylate resin, polystyrene resin, etc.). Among the plastics, materials having a polar group within molecules which have a tendency of molecular polarization (Examples: polytetrafluoroethylene resin, polyamide resin, polycarbonate resin, epoxy resin, etc.) cause the inner surface of the tip to be blackened to deteriorate the light irradiating performance.

On the other hand, a tip made of polyacetal resin known as Derlin (a trademark of Du Pont) has a possibility to generate formalin which is injurious to the living body due to the thermal decomposition by laser.

As described above, it is necessary to select very carefully a tip for diffusion of a pulse laser beam different from a continuous wave laser.

SUMMARY OF THE INVENTION

It is an object of the present invention to provide a fiber optic laser conducting and diffusion device for a photodynamic therapy using a pulse wave laser beam which is stable in use and high in safety.

The present invention has been developed as a result of various experiments and studies. The present invention provides a fiber optic laser conducting and diffusion device for a photodynamic therapy characterized in that a light diffusion tip made of polyolefin resin, which is less subjected to decomposition due to a pulse wave laser, surface blackening, and generation of dangerous substances due to decomposition by laser energy, because a pulse laser beam being conducted by optical fibers is irradiated against a specific object, is attached to an end of the optical fiber.

The polyolefin resin-made light diffusion tips include tips made of, for example, polypropylene resin, polybutylene resin, polypentene resin, polyethylene resin, etc. The tip made of polyethylene resin is particularly preferable.

The polyolefin resin is a high polymer of hydrocarbon having a composition of $C_nH_{2n}$ main chain, which is high in chemical stability, has an appropriate hardness, is not decomposed due to the shock wave of a pulse laser, is not subjected to blackening because it has a good molecular symmetry and has no polarity group, and generates no dangerous substance due to thermal decomposition because it is a simple straight-chain hydrocarbon high polymer.

This polyolefin resin has properties such that, when it is slowly cooled during molding and cooling from a melt, molecular spherulites are generated. When the molecular spherulites are grown to a size in excess of the wavelength of a ray of light, they become whitened so as to exhibit a light diffusion function. The present invention is characterized by the use of a light diffusion tip made of polyolefin resin having the generated molecular spherulites by making use of the aforementioned properties.

The generating state of molecular spherulites is considerably freely changed by the control of the slow-cooling temperature, as well as by the selection of heat-treating conditions of the molded tip. Therefore, the controllability of a degree of light diffusion is excellent as compared with the conventional method in which it is necessary to add and mix light diffusion particles.

In order to increase the quantity of irradiated light, it is effective to provide a light reflecting mirror on the inner surface of a hollow portion of the tip. Further, the internal surface of the tip can be incised; a clad at the extreme end of the optical fiber in the tip can be removed to for improved exposure and the surface thereof can be roughened; and the light irradiating end of a core can be roughened. These are effective means to make the irradiating light uniform.

DESCRIPTION OF THE PREFERRED EMBODIMENTS

Figure 1:
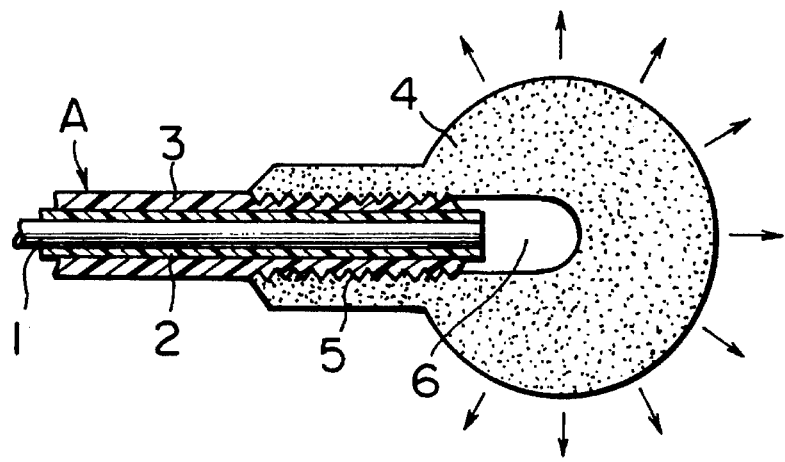
FIG. 1 is a sectional view of a whole directional irradiating type device according to an embodiment of the present invention.

FIG. 1 shows an embodiment of a whole-directional irradiating type device according to the present invention.

As an optical fiber A, use is made of a hard clad PCS, Toray (K.K.) HNS. FB400 (core diameter: 400 μm). Reference numeral 1 designates a core; 2 a plastic clad; 3 a plastic jacket; 4 a polyethylene light diffusion tip having generated molecular spherulites; 5 a threaded portion threaded between the plastic jacket 3 and the tip 4 and adhered and fixed with epoxy resin; and 6 a hollow portion.

Figure 2:
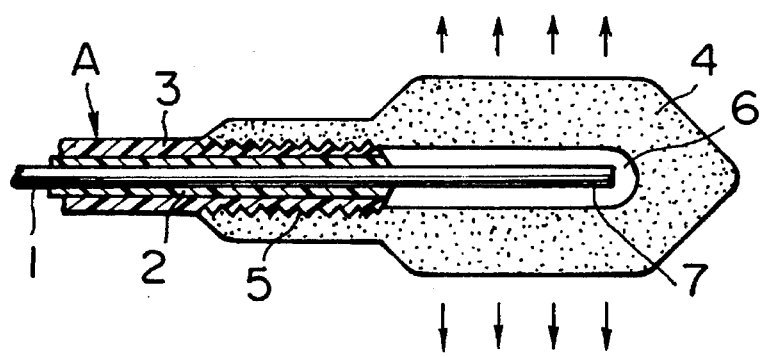
FIG. 2 is a sectional view of of a side-directional irradiating type device according to an embodiment of the present invention.

FIG. 2 shows an embodiment of a side-directional exit type device according to the present invention. A plastic clad at the extreme end of the optical fiber A is removed to expose a core end portion 7 to increase the irradiating light.

Figure 3:
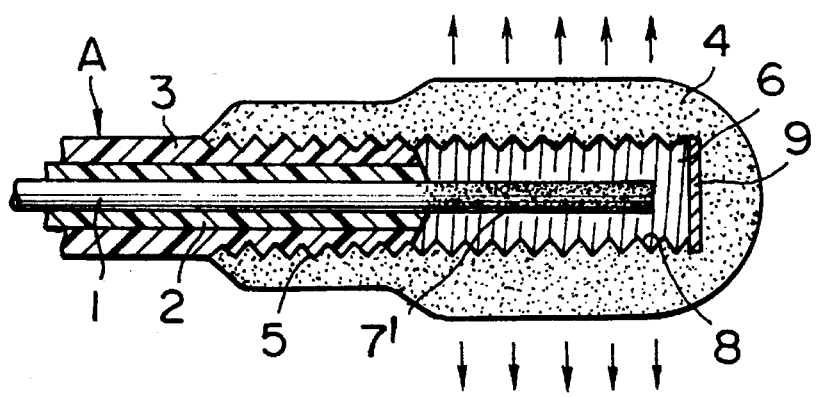
FIG. 3 is a sectional view of a further side-directional irradiating type device according to an embodiment of the present invention.

FIG. 3 shows a further embodiment of a side-directional exit type device according to the present invention. A sand-blast processing is applied to the extreme end 7 of the core 1 with the plastic clad removed to roughen the surface so as to make the irradiating light uniform. Reference numeral 8 designates a tip inner surface portion spirally formed to provide incisions for the light diffusion, and reference numeral 9 designates a light reflecting mirror.

Figure 4:
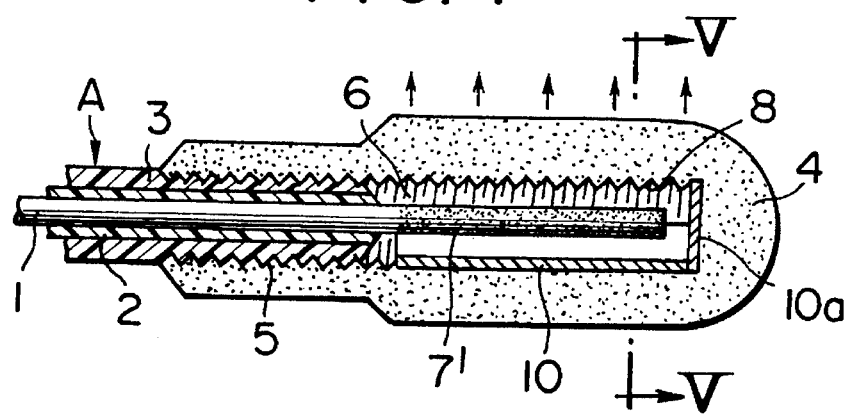
FIG. 4 is a sectional view of an embodiment of another side-directional irradiating type device according to an embodiment of the present invention.
Figure 5:
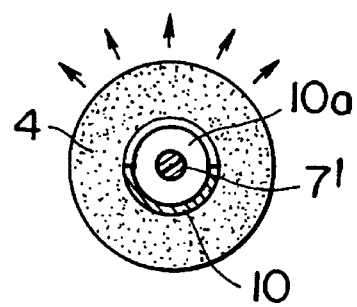
FIG. 5 is a sectional view taken on line V—V of FIG. 4.

FIGS. 4 and 5 show another embodiment of a side-directional exit type device according to the present invention. A reflecting mirror 10 is provided on the inner surface of the tip 4 so as to oppose a side portion and an extreme end portion of a core end portion 7' exposed and with the surface thereof roughened. According to this embodiment, irradiating light quantities further increase.

Figure 6:
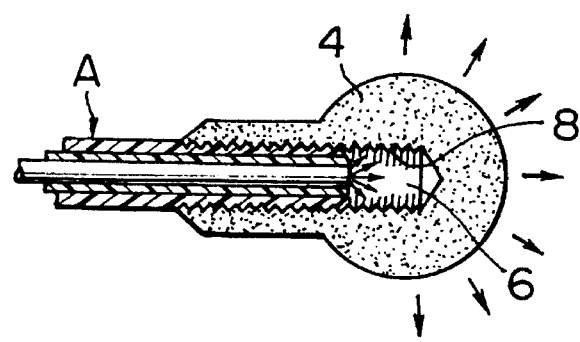
FIG. 6 is a sectional view of a further whole-directional irradiating type device according to an embodiment of the present invention.
Figure 7:
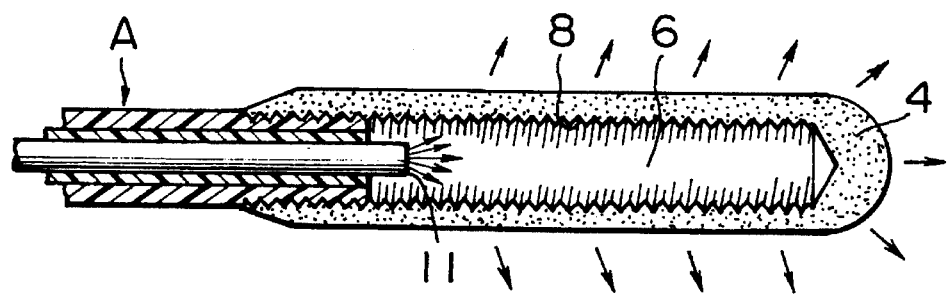
FIG. 7 is a sectional view of another side-directional irradiating type according to an embodiment of the present invention.

FIGS. 6 and 7 shows arrangement wherein the fiber end is roughened to make an irradiating light uniform as a diffusion light. FIG. 6 shows a whole-directional irradiating type device, and FIG. 7 shows a side-directional irradiating type device.

In the embodiments described above, a tip having an outside diameter of 1.5 mm was fabricated. An eximer laser beam of 630 nm was diffused in the amount of 600 J in total with 4 to 8 mJ/pulse, 40 to 80 Hz operation. The irradiating light was uniform. Damage in tip, and lowering in light quantities due to blackening were not observed. According to the configuration of the present invention, it is possible to provide fiber optic laser conducting and diffusion device for a photodynamic therapy by a pulse wave laser beam of high safety.

What is claimed is:

1. A fiber optic laser conducting and diffusion device for a photodynamic therapy characterized in that a polyolefin resin light diffusion tip is attached to an optical fiber end to irradiate a pulse laser beam conducted in the optical fiber against an object, and wherein a light reflecting mirror is provided in a hollow portion of the polyolefin resin light diffusion tip.

2. A fiber optic laser conducting and diffusion device for a photodynamic therapy according to claim 1, wherein the polyolefin resin light diffusion tip is a polyethylene resin light diffusion tip.

3. A fiber optic laser conducting and diffusion device for a photodynamic therapy characterized in that a polyolefin resin light diffusion tip is attached to an optical fiber end to irradiate a pulse laser beam conducted in the optical fiber against an object, and wherein a light reflecting mirror is provided in a hollow portion of the polyolefin resin light diffusion tip.

4. A fiber optic laser conducting and diffusion device for a photodynamic therapy according to claim 3, wherein the polyolefin resin light diffusion tip is a polyethylene resin light diffusion tip.

5. A fiber optic laser conducting and diffusion device for use attached to an end of an optical fiber for performing photodynamic therapy, said fiber optic laser conducting and diffusion device comprising:

a light diffusion tip for diffusing light from the optical fiber irradiated toward an object; and wherein said light diffusion tip is formed of polyolefin resin having generated molecular spherulites.

6. A fiber optic laser conducting and diffusion device according to claim 5, wherein said light diffusion tip has a hollow portion formed therein; and a light reflecting mirror is provided in said hollow portion of said light diffusion tip.

7. A fiber optic laser conducting and diffusion device according to claim 5, wherein said light diffusion tip has an inner surface; and light reflecting and diffusion incisions are formed in said inner surface of said light diffusion tip.

8. A fiber optic laser conducting and diffusion device according to claim 5, wherein said light diffusion tip has a hollow portion formed therein;

a core portion of the end of the optical fiber projects into said hollow portion and is exposed to an inner surface of said light diffusion tip; and an outer surface of said core portion projecting into said hollow portion is roughened.

9. A fiber optic laser conducting and diffusion device according to claim 8, wherein said polyolefin resin of which said light diffusion tip is formed comprises polyethylene resin.

10. A fiber optic laser conducting and diffusion device according to claim 5, wherein said polyolefin resin of which said light diffusion tip is formed comprises polyethylene resin.

\* \* \* \* \*